US005795770A

United States Patent [19]

Gaber

[11] Patent Number: 5,795,770
[45] Date of Patent: Aug. 18, 1998

[54] GENETICALLY ENGINEERED EUKARYOTIC ORGANISM CAPABLE OF DETECTING THE EXPRESSION OF HETEROLOGOUS ION CHANNELS AND METHOD TO USE THE SAME

[75] Inventor: Richard F. Gaber, Wilmette, Ill.

[73] Assignee: Northwestern University, Evanston, Ill.

[21] Appl. No.: 795,788

[22] Filed: Feb. 5, 1997

Related U.S. Application Data

[63] Continuation of Ser. No. 923,094, Jul. 31, 1992, abandoned, which is a continuation-in-part of Ser. No. 874,846, Apr. 27, 1992, abandoned.

[51] Int. Cl.$^6$ .............................. C12N 1/19; C12N 1/18; C12N 15/29
[52] U.S. Cl. ................................ 435/254.2; 435/254.21; 435/320.1; 435/172.3; 435/29; 536/23.6
[58] Field of Search ........................... 435/254.2, 254.21, 435/320.1, 172.3, 29; 536/23.6

[56] References Cited

U.S. PATENT DOCUMENTS

| | | | |
|---|---|---|---|
| 4,675,285 | 6/1987 | Clark et al. | 435/6 |
| 4,745,065 | 5/1988 | Delcour et al. | 435/256 |
| 4,971,908 | 11/1990 | Kishore et al. | 435/172.1 |

FOREIGN PATENT DOCUMENTS 9202634  2/1992  WIPO.

OTHER PUBLICATIONS

Anderson et al., "Structural and functional conversation between the high-affinity K+ transporters of *Saccharomyces uvarum* and *Saccharomyces cerevisiae*" *Gene* 99:39–46 (1991).
Anderson et al., "Functional expression of a probably *Arabidopsis thaliana* potassium channel in *Saccharomyces cerevisiae*" *Proc. Natl. Acad. Sci. USA* 89:3736–3740 (1992).
Armstrong, "Interaction of Tetraethylammonium Ion Derivatives with the Pottasium Channels of Giant Axons" *J. Gen. Physio.* 58:413–437 (1971).
Becker et al. "[12]High-Efficiency Transformation of Yeast by Electroporation" *Methods in Enzymology* 194:182–187 (1991).
Burgers et al. "Transformation of Yeast Spheroplasts without Cell Fusion" *Analy. Biochem.* 163:391–397 (1987).
Butler et al. "A Family of Putative Potassium Channel Genes in Drosphila" *Science* 243:943–947 (1989).
Chandy, et al. "A Family of Three Mouse Potassium Channel Genes with Intronless Coding Regions" *Science* 247:973–975 (1990).
Doy et al. "Transgenosis of Bacterial genes from *Escherichia Coli* to cultures of Haploid Lycopersicon Esculentum and Haploid Arabidopsis Thaliana Plant Cells" *Bacterial Genes Expressed in Plant Cells* pp. 21–37 (1972).
Elledge et al. "λYES: A multifunctional cDNA expression vector for the isolation of genes by complementation of yeast and *Escherichia coli* mutations" *Proc. Natl. Acad. Sci. USA* 88:1731–1735 (1991).
Feinberg, A.P., et al., "A Technique for Radiolabeling DNA Restriction Endonuclease Fragments to High Specific Activity" Analytical Biochemistry 132:6–13 (1983).
Frech, G.C., et al., "A novel potassium channel with delayed rectifier properties isolated from rat brain by expression cloning" Nature 340:642–645 (1989).
Gaber, R.F., et al., "TrK1 Encodes Plasma Membrane Protein Required for High–Affinity Potassium Transport in *Saccharomyces cerevisiae*, " Molecular and Cellular Biology 8:2848–2859 (1988).
Greenblatt, R.E., et al., "The structure of voltage–sensitive sodium channel." FEBS Lett. 193:125–134 (1985).
Gustin, M.C., et al., "Ion Channels in Yeast," Science 233:1195–1197 (1986).
Guy, H.R., et al., "Molecular model of the action potential sodium channel." Proc. Natl. Acad. Sci. USA 83:508–512 (1986).
Hille, B., "The Selective Inhibition of Delayed Potassium Currents in Nerve by Tetraethylammounium Ion." J. Gen. Physiol. 50:1287–1302 (1967).
Hopp, T.P., et al., "Prediction of protein antigenic determinants from amino acid sequences." Proc. Natl. Acad. Sci. USA 78:3824–3828 (1981).
Hoshi, T., et al., "Biophysical and Molecular Mechanisms of Shaker Potassium Channel Inactivation." Science 250:533–538 (1990).
Jan, L.Y., et al., "Voltage–Sensitive Ion Channels." Cell 56: 13–25 (1989).
Ko, C.H., et al. I, "TRK2 is Required for Low Affinity K$^+$ Transport in *Saccharomyces cerevisiae*," Genetics 125:305–312 (1990).
Ko, C.H., et al. II, TRK1 and TRK2 Encode Structurally Related K$^+$ Transporters in *Saccharomyces cerevisiae*, Mol. Cell. Biol. 11:4266–4273 (1991).
Kochian, L.V., et al.,"High Affinity K$^+$ Uptake in Maize Roots," Plant Physiol. 91:1202–1211 (1989).
Lewin, B., "Dealing with DNA," and Transposable Elements in Bacteria, Genes pp. 300–333 and 589–631 (1983).

(List continued on next page.)

*Primary Examiner*—Rebecca E. Prouty
*Attorney, Agent, or Firm*—Dressler, Rockey, Milnamow & Katz, Ltd.

[57] ABSTRACT

This invention relates to genetically engineered eukaryotic organisms, such as yeast, that are made capable of detecting the expression of heterologous ion channels. These organisms include a potassium transport defective phenotype eukaryotic organism transformed with DNA that suppresses the potassium transport defective phenotype in the organism. A potassium transport gene is set out in Sequence Id. No. 1. This genetically engineered organism can be used to screen for new herbicides or drugs.

5 Claims, 3 Drawing Sheets

OTHER PUBLICATIONS

MacKinnon, R., et al., "Mutations Affecting TEA Blockade and Ion Permeation in Voltage–Activated K$^+$ Channels." Science 250:276–279 (1990).

Noda, M., et al., "Primary structure of *Electrophorus electricus* sodium channel deduced from cDNA sequence." Nature 312:121–127 (1984).

Rodriguez–Navarro, A., et al., "A Potassium–Proton Symport in *Neurospora crassa*." J. Gen. Physiol. 87:649–674 (1986).

Sanger, F., et al., "DNA sequencing with chain–terminating inhibitors." Proc. Natl. Acad. Sci. USA 74:5463–5467 (1977).

Sauer, B., et al., "The cyclization of linear DNA in *Escherichia coli* by site–specific recombination," Gene 70:331–341 (1988).

Schroeder, J.I., et al., "Involvement of ion channels and active transport in osmoregulation and signaling of higher plant cells." TIBS 14:187–192 (1989).

Schwarz, T.L., et al., "Multiple potassium–channel components are produced by alternative splicing at the Shaker locus in Drosophila." Nature 331:137–142 (1988).

Serrano, R., "Plasma Membrane ATPase of Fungi and Plants as a Novel Type of Proton Pump," Curr. Top. Cell. Regul. 23:87–126 (1984).

Sikorski, R.S., et al., "A System of Shuttle Vectors and Yeast Host Strains Designed for Efficient Manipulation of DNA in *Saccharomyces cerevisiae*," Genetics 122:19–27 (1989).

Sternberg, N., "The P1 lox–Cre site–specific recombination system: properties of lox sites and biochemistry of lox–Cre Interactions." UCLA Symposia on Molecular & Cellular Biology, vol. 10:671–684 (1983).

Tanabe, T., "Primary structure of the receptor for calcium channel blockers from skeletal muscle," Nature 328:313–318 (1987).

Tempel, B.L., et al. I"Cloning of a probable potassium channel gene from mouse brain." Nature 332:837–839 (1988).

Tempel, B.L., et al. II "Sequence of a Probable Potassium Channel Component Encoded at Shaker Locus of Drosophila." Science 237:770–775 (1987).

Yellen, G., et al., "Mutations Affecting Internal TEA Blockade Identify the Probable Pore–Forming Region of a K$^+$ Channel," Science 251:939–942 (1991).

Yool, A.J., et al., "Alteration of ionic selectivity of a K$^+$ channel by mutation of the H5 region," Nature 349:700–704 (1991).

Zagotta, W.N., et al., "Restoration of Inactivation in Mutants of Shaker Potassium Channels by a Peptide Derived from ShB." Science 250:568–571 (1990).

Sanguinetti et al. 1990. J. Gen. Physiol. 96: 195–215.

Singleton, P. 1988. *Dictionary of Microbiology and Molecular Biology*, Antey Rowe Intl., Wiltshire, Great Britain, p. 420.

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 2173 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:1:

```
CCGAATTCCT   CGAGCTACGT   CAGGGAAAAG   ATGTCGATCT   CTTGGACTCG   AAATTTCTTC        60

GAAAGATTCT   GCGTCGAGGA   ATACAATATA   GACACCATAA   AACAGAGTAG   TTTCCTCTCT       120

GCCGATCTTC   TACCATCTCT   TGGAGCCAGG   ATCAACCAAT   CTACTAAGCT   CCGCAAACAC       180

ATAATCTCTC   CTTTTAATCC   ACGTTACAGA   GCGTGGGAGA   TGTGGCTAGT   ATTACTAGTT       240

ATTTACTCAG   CTTGGATTTG   CCCATTTCAA   TTTGCTTTCA   TCACCTATAA   AAAAGACGCG       300

ATTTTCATCA   TCGACAACAT   TGTTAATGGC   TTCTTCGCCA   TTGATATTAT   TCTCACCTTC       360

TTCGTCGCTT   ATCTCGATAG   CCACTCCTAT   CTTCTAGTTG   ACAGTCCTAA   GAAAATAGCA       420
```

-continued

```
ATAAGGTACC TTTCGACGTG GTTCGCTTTC GATGTTTGTT CCACAGCACC ATTTCAGCCA      480
CTAAGCCTCT TGTTTAACTA CAACGGAAGC GAACTAGGAT TCAGAATTCT TAGCATGCTC      540
AGGTTATGGC GTCTCCGGCG AGTTAGCTCG CTATTGCAA GGCTTGAGAA AGATATCCGT       600
TTCAACTATT TCTGGATACG TTGCACAAAA CTCATTTCGG TCACTTTGTT CGCTATACAT      660
TGTGCTGGAT GTTCAACTA CCTGATTGCA GATAGATATC CTAATCCAAG AAAGACATGG       720
ATTGGAGCTG TGTATCCAAA TTTCAAAGAA GCAAGTCTAT GGAATAGATA TGTGACTGCT      780
CTTTACTGGT CCATTACGAC ATTAACGACC ACGGGATATG GAGATTTTCA TGCTGAGAAC      840
CCAAGAGAAA TGCTTTTTGA CATTTTCTTC ATGATGTTCA ACCTCGGTTT GACAGCTTAC      900
CTCATTGGAA ATATGACCAA CCTCGTCGTT CATTGGACTA GCCGAACCAG AACCTTTAGG     960
GATTCAGTGA GAGCTGCTTC AGAGTTTGCT TCAAGAAATC AACTCCCACA TGACATACAA     1020
GATCAAATGT TATCACACAT TTGCTTAAAG TTCAAAACAG AGGGCTTGAA ACAACAAGAG    1080
ACCTTGAACA ATCTGCCAAA AGCAATCCGG TCAAGCATTG CAAACTATTT ATTCTTCCCC    1140
ATTGTTCACA ACATTTACCT CTTTCAAGGA GTTTCTCGTA ACTTCCTCTT TCAATTGGTT    1200
TCAGATATAG ACGCTGAGTA TTTCCCACCA AAAGAAGATA TAATTCTACA AAACGAAGCT    1260
CCTACTGATC TTTACATTCT GGTGTCAGGA GCAGTGGACT TCACTGTCTA CGTTGATGGA    1320
CATGATCAGT TTCAAGGGAA AGCAGTAATT GGAGAAACAT TTGGAGAGGT TGGAGTTTTA    1380
TACTATAGAC CACAACCATT CACAGTAAGA ACAACCGAGC TATCTCAAAT ACTGCGGATA    1440
AGCAGAACAT CGCTGATGAG TGCGATGCAT GCTCATGCTG ACGATGGACG AGTCATCATG    1500
AACAATCTCT TCATGAAACT TAGAGGGCAA CAGTCAATAG CAATAGATGA TTCGAATACT    1560
AGTGGTCACG AAAACAGAGA TTTCAAAAGC ATGGGATGGG AAGAGTGGAG AGATTCAAGA    1620
AAAGATGGCT ATGGTTTAGA TGTTACGAAT CCGACTTCCG ACACTGCTCT AATGGATGCG    1680
ATTCACAAGG AAGATACTGA AATGGTTAAG AAGATACTTA AGGAACAAAA GATAGAGAGA    1740
GCCAAAGTGG AAAGATCAAG TAGTGAAACC GCTGGAAGAA GTTACGCTAA CGATTCATCG    1800
AAAAAAGATC CATATTGCAG CTCAAGCAAC CAAATCATCA AGCCATGCAA ACGAGAAGAA    1860
AAGAGAGTTA CCATCCACAT GATGTCTGAG AGCAAGAACG GGAAGTTGAT ACTCTTACCA    1920
TCATCCATAG AAGAGCTTCT AAGACTTGCA AGTGAGAAGT TTGGAGGCTG CAACTTCACA    1980
AAGATCACCA ATGCGGACAA CGCTGAGATT GATGATTTAG ATGTCATTTG GGATGGTGAT    2040
CATTTGTATT TTTCATCAAA TTGAGTTTGA AAACTCGACT TCATTTATAG AGCATGTATA    2100
TCTGCAGATA ATGTATTTTT ACCCGGTTTC ATAGAAAAGT CTAGATTATC CCCTGACGTA    2160
GCTCGAGGAA TTC                                                        2173
```

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:2:

```
TACTTTAACG TCAAGGAG                                                      18
```

( 2 ) INFORMATION FOR SEQ ID NO:3:

( i ) SEQUENCE CHARACTERISTICS:

-continued ( A ) LENGTH: 17 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:3:

CTAAGCTCCG CAAACAC                                                                                                17

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:4:

CTTCTAGTTG ACAGTC                                                                                                 16

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:5:

CGGAAGCGAA CTAGG                                                                                                  15

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:6:

CATTGTGCTG GATGT                                                                                                  15

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:7:

GATGTTCAAC CTCGG                                                                                                  15

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:8:

TACTGCGGAT AAGCA                                                                                           15

( 2 ) INFORMATION FOR SEQ ID NO:9:

( i ) SEQUENCE CHARACTERISTICS:
                ( A ) LENGTH: 15 base pairs
                ( B ) TYPE: nucleic acid
                ( C ) STRANDEDNESS: unknown
                ( D ) TOPOLOGY: unknown ( i i ) MOLECULE TYPE: DNA (genomic)

( x i ) SEQUENCE DESCRIPTION: SEQ ID NO:9:

GGATGGGAAG AGTGG                                                                                           15

( 2 ) INFORMATION FOR SEQ ID NO:10:

( i ) SEQUENCE CHARACTERISTICS:
                ( A ) LENGTH: 15 base pairs
                ( B ) TYPE: nucleic acid
                ( C ) STRANDEDNESS: unknown
                ( D ) TOPOLOGY: unknown ( i i ) MOLECULE TYPE: DNA (genomic)

( x i ) SEQUENCE DESCRIPTION: SEQ ID NO:10:

TAGTGAAACC GCTGG                                                                                           15

( 2 ) INFORMATION FOR SEQ ID NO:11:

( i ) SEQUENCE CHARACTERISTICS:
                ( A ) LENGTH: 15 base pairs
                ( B ) TYPE: nucleic acid
                ( C ) STRANDEDNESS: unknown
                ( D ) TOPOLOGY: unknown ( i i ) MOLECULE TYPE: DNA (genomic)

( x i ) SEQUENCE DESCRIPTION: SEQ ID NO:11:

ATCCATAGAA GAGCT                                                                                           15

( 2 ) INFORMATION FOR SEQ ID NO:12:

( i ) SEQUENCE CHARACTERISTICS:
                ( A ) LENGTH: 15 base pairs
                ( B ) TYPE: nucleic acid
                ( C ) STRANDEDNESS: unknown
                ( D ) TOPOLOGY: unknown ( i i ) MOLECULE TYPE: DNA (genomic)

( x i ) SEQUENCE DESCRIPTION: SEQ ID NO:12:

GCATGTATAT CTGCA                                                                                           15

( 2 ) INFORMATION FOR SEQ ID NO:13:

( i ) SEQUENCE CHARACTERISTICS:
                ( A ) LENGTH: 15 base pairs
                ( B ) TYPE: nucleic acid
                ( C ) STRANDEDNESS: unknown
                ( D ) TOPOLOGY: unknown ( i i ) MOLECULE TYPE: DNA (genomic)

( x i ) SEQUENCE DESCRIPTION: SEQ ID NO:13:

GCTGAGTAAA TAACT                                                                                           15

( 2 ) INFORMATION FOR SEQ ID NO:14:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:14:

ATTCGTATTT TCTTA                                                                  15

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:15:

TCAAGCCTTG CAAAT                                                                  15

( 2 ) INFORMATION FOR SEQ ID NO:16:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:16:

TGCTTCTTTG AAATT                                                                  15

( 2 ) INFORMATION FOR SEQ ID NO:17:

( i ) SEQUENCE CHARACTERISTICS:
        ( A ) LENGTH: 19 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:17:

AGGTTGGTCA TATTTCCAA                                                          19

( 2 ) INFORMATION FOR SEQ ID NO:18:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:18:

TTGTTCTTAC TGTGA                                                                  15

( 2 ) INFORMATION FOR SEQ ID NO:19:

( i ) SEQUENCE CHARACTERISTICS:

(A) LENGTH: 17 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:19:

GTCGGAAGTC GGATTCG  17

(2) INFORMATION FOR SEQ ID NO:20:

(i) SEQUENCE CHARACTERISTICS:
        (A) LENGTH: 15 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:20:

GGTTGCTTGA GCTGC  15

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:21:

ACCATCCCAA ATGACAT  17

(2) INFORMATION FOR SEQ ID NO:22:

(i) SEQUENCE CHARACTERISTICS:
        (A) LENGTH: 17 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:22:

TGTGGAATTG TGAGCGG  17

GENETICALLY ENGINEERED EUKARYOTIC ORGANISM CAPABLE OF DETECTING THE EXPRESSION OF HETEROLOGOUS ION CHANNELS AND METHOD TO USE THE SAME

This is a continuation of application Ser. No. 07/923,094, filed Jul. 31, 1992, now abandoned which is a continuation-in-part of U.S. Ser. No. 874,846 filed April 27, 1992.

This invention was made with government support under grant No. DCB8711346 awarded by National Science Foundation and grant No. 90-37261-5411 awarded by U.S. Dept. of Agriculture. The government has certain rights in the invention.

BACKGROUND OF THE INVENTION

1. Field of the Invention

This invention relates to genetically engineered eukaryotic organisms, such as yeast, that are made capable of detecting the expression of heterologous ion channels. This genetically engineered organism can be used to screen for new herbicides or pharmaceuticals.

2. Description of Prior Work in the Field

Advances in molecular biology have provided the means to transform organisms to contain foreign genes. Such genes can be transformed into the organism to affect its function. B. Lewin, Genes, 300–333 and 589–631 (1983) (hereby incorporated by reference).

In plants and fungi the uptake and intracellular concentration of potassium serve a variety of vital functions including the control of cell shape and turgor, the establishment of an ionic milieu compatible with enzyme function, and the enhancement of plasma membrane proton pump function. Serrano, R. *Plasma Membrane ATPase of Fungi and Plants as a Novel Type of Proton Pump*; Curr. Top. Cell. Regul. 23:87–126 (1984).

The inventor and other colleagues from Northwestern University have cloned two genes TRK1 and TRK2 that encode potassium transporters in *Saccharomyces cerevisiae*. The TRK2 gene encodes a low-affinity and the TRK1 gene encodes for a high-affinity potassium transporter. Cells deleted for both TRK1 and TRK2 are hypersensitive to low pH. They are also severely limited in their ability to take up potassium. Ko et al. *TRK1 and TRK2 Encode Structurally Related Potassium Transporter in Saccharomyces cerevisiae*, Molec. and Cell. Bio. 11:4266–4273 (Aug. 1991) (hereby incorporated by reference); Ko et al. *TRK2 is Required for Low Affinity $K^+$ Transport in Saccharomyces Cerevisiae*, Genetics 125:305–312 (June 1990) (hereby incorporated by reference).

Herbicide and drug identification frequently involves the detection of single compounds that show potential as plant growth inhibitors and/or pharmaceuticals from large numbers of naturally occurring and synthetic substances. A disadvantage of current identification processes is that they can be time consuming and expensive. Also, not all commonly used screening procedures demonstrate a specific mode of action of the active compounds.

The present invention relates to method for drug and herbicide testing that may significantly reduce assay time and cost. A unique feature of this method is its capacity to reveal the specific molecular system affected by the assayed compounds.

SUMMARY OF THE INVENTION

The invention consists of a microbial system that can serve as a sceen for compounds that inhibit potassium channels. Specifically, a genetically engineered strain of yeast, rendered defective in potassium uptake and supplied with a plant gene has been developed by the inventor. The altered yeast strain has been shown to be effective as a cell culture system for screening potassium channel-inhibiting compounds.

More specifically, the present invention provides a genetically engineered organism that includes a potassium transport defective phenotype. More specifically, this invention provides a genetically engineered yeast strain (ATCC No. 74144 deposited Mar. 25, 1992 with the American Type Culture Collection, 12301 Parklawn Drive, Rockville, Md. 20852) that is deleted for both of its endogenous potassium transporters (TRK1 and TRK2) and which includes a plasmid expressing a heterologous plant potassium channel gene from *Arabidopsis thaliana*. These yeast cells can be used for rapid screening of chemical compounds for anti-potassium channel activity by measuring a compound's ability to inhibit the growth of the genetically engineered yeast cells. These compounds may have activity as a herbicide or pharmaceutical.

Additionally, this invention provides cDNA for a potassium channel gene. This cDNA sequence is shown in Sequence Id. No. 1 and is incorporated into a plasmid identified as ATCC No. 75224, which plasmid is also contained in the cells of ATCC 74144. Both of these deposits were made on Mar. 25, 1992 with American Type Culture Collection, Rockville, Md., pursuant to the Budapest Treaty, and viability was confirmed on Mar. 27, 1992. This gene can be used to make a genetically engineered eukaryotic organism capable of detecting heterologous ion channels. This organism can be made by transfecting a potassium transport defective phenotypic organism with DNA that suppresses the potassium transport defective phenotype in the organism.

More specifically, this invention provides a genetically engineered eukaryotic organism dependent on a heterologous ion channel for growth. The organism has the characteristics of the strain deposited as ATCC No. 74144. This organism is a *Saccharomyces cerevisiae* deleted for TRK2 and TRK1, or only TRK1, that is transfected with the DNA sequence set out in the Sequence Id. No. 1. As deposited with the ATCC, the yeast cells have both the trk1 and trk2 genes deleted.

Still, additionally, this invention provides a method to screen compounds for their ability to inhibit potassium transport in vivo. This screening method involves: adding the compound to be screened to a genetically engineered organism capable of detecting heterologous ion channel wherein the organism is a potassium transport defective phenotypic organism transformed with DNA that suppresses the potassium transport defective phenotype in the organism, to a media containing potassium, and determining whether the organism's growth is inhibited.

DETAILED DESCRIPTION OF THE INVENTION AND BEST MODE

Figure 1:
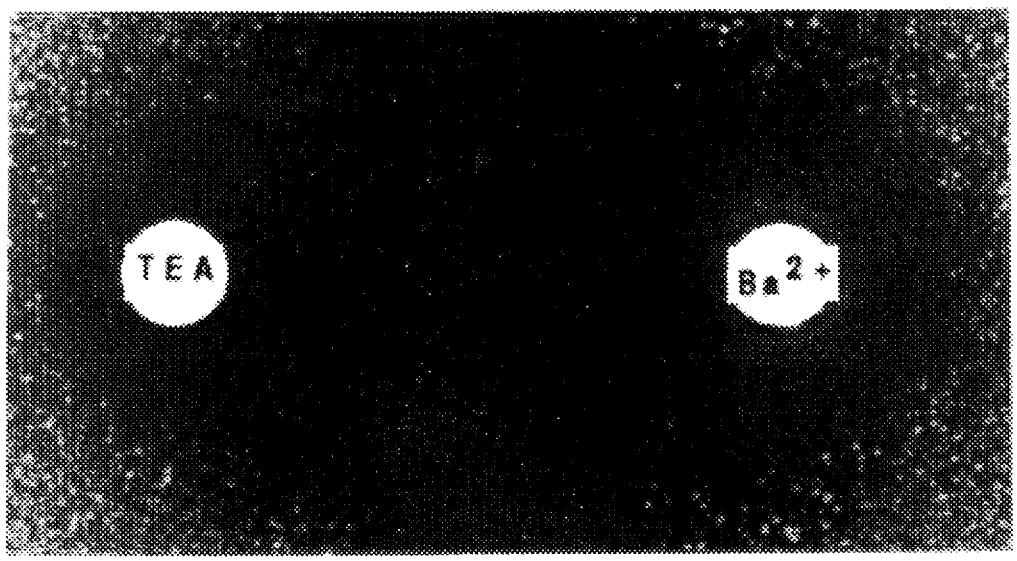
FIG. 1 shows TEA and $BA^{2+}$ inhibition of KAT1 in vivo. Approximately $10^5$ CY162/pKAT1 cells were plated on to GAL-URA 0.2K solid media. 20 μl of 1M TEA and 20μl of 1M $BaCl_2$ were applied to sterile filter disks placed on the media; a halo of inhibited cell growth can be seen around the filters on the 0.2 mM $K^+$ containing plate. $BaCl_2$ precipitated out of the medium in the region surrounding the $Ba^{2+}$ filter disk.

The present invention provides a genetically engineered organism capable of detecting heterologous ion channels and a method to use the same in screening for new herbicide or drug compounds. The term "heterologous" in this context means the expression in *Saccharomyces cerevisiae* of any non*Saccharomyces cerevisiae* gene, i.e. any ion channel gene from another organism. More specifically, this invention provides a yeast strain deleted for both of its endogenous potassium transporters TRK1 and TRK2 and that includes the newly discovered heterologous plant potassium channel gene (Sequence Id. No. 1) from *Arabidopsis thaliana* deposited with the ATCC under the Budapest Convention and that has received ATCC numbers 74144 and 75224. It should be noted, however, that a genetically engineered yeast stain deleted for TRK1 and including the plant potassium channel gene from *Arabidopsis thaliana* is also contemplated by this invention. The altered yeast strain has been shown to be effective as a cell culture system for screening potassium channel-inhibiting compounds. The system is easily adaptable to microtiter plate technology rendering the method rapid and inexpensive. Cell growth and inhibition as determined by turbidity, can be measured by standard spectrophotometric instrumentation. The identification of compounds that both completely and partially inhibit potassium channel activity is also possible. The present yeast strain containing the plant gene is useful for screening pharmaceuticals because all potassium channels are sensitive to the same compounds; thus, if a compound was identified as having a potassium channel inhibiting activity it could be further tested for likely pharmaceutical utility.

In the present invention, the endogenous TRK1 (or TRK1 and TRK2) transporters are deleted in order to 1) detect function of the heterologous ion channel and 2) to make the strain dependent on the heterologous channel for growth. It should be noted, however, that one would not need to delete TRK1 (or TRK1 and TRK2) in order to make the *S. cerevisiae* cells dependent on the heterologous potassium channels for growth. One could simply isolate uncharacterized mutations in these that have the effect of significantly reducing their function. As such these organisms include a potassium transport defective phenotype transformed with DNA that suppresses the potassium transport defective phenotype in the organism.

It should be noted, however, that other potassium-transporting proteins, (not just those known to function as channels) could also suppress the potassium transport defect in trk1Δ trk2Δ cells since these proteins could also represent essential plant proteins and thus, be useful in the screening process for new herbicides or drugs. The KAT1 gene has the following characteristics: 1) KAT1 suppresses the Trk- phenotype of *S. cerevisiae* cells deleted for their endogenous potassium transporters; 2) the inferred protein sequence includes a cluster of six putative membrane-spanning domains and conserved amino acids sequences corresponding to the presumptive voltage-sensing (S4) and pore-forming (SS1-SS2 or H5) regions; and 3) potassium channel-specific blockers (TEA and $Ba^{2+}$) inhibit of KAT1 in vivo. Alternatively, *Schizosaccharomyces pombe*, could be transformed with pKAT1 due to the presence of the *Saccharomyces cerevisiae* selectable marker URA3.

The gene that encodes for the plant potassium gene was identified as follows:

1. Media and Strains

YNB and LS media were prepared as described by Sherman et al. and Gaber etal (Sherman, F., Fink, G. R. and Hicks, J. (1986) (hereby incorporated by reference) Methods in Yeast Genetics, Cold Spring Harbor Laboratory, Cold Spring Harbor, N.Y.; Gaber, R. F., Styles, C. A. and Fink, G. R. (1988) Mol. Cell. Biol. 8, 2848–2859). AA-URA is medium supplemented with all amino acids and nucleosides except uracil. Media with galactose or glucose as the sole carbon source are indicated as GAL and GLU. Ko and Gaber describe construction of the *S. cerevisiae* strain, CY162, MATα ura3-52 trk1Δ his3 200 his4-15 trk2Δ 1::pCK64 (Ko, C. H. and Gaber, R. F. (1991) Mol. Cell. Biol. 11:4266–4273). Yeast transformation was performed by electroporation (Becker, D. M. and Guarente, L. (1991) Meth. Enzym. 194, 182–187). Plasmids were selected and propagated in *E. coli* strain HB101 on Luria broth (LB) medium supplemental with 50 µg/ml ampicillin. LB medium is used to grow *E. Coli*. LB medium and ampicillin is used to maintain selection for the presence of ampicillin resistance-conferring plasmids in *E. Coli* like pKAT1.

2. cDNA Cloning

Figure 3:
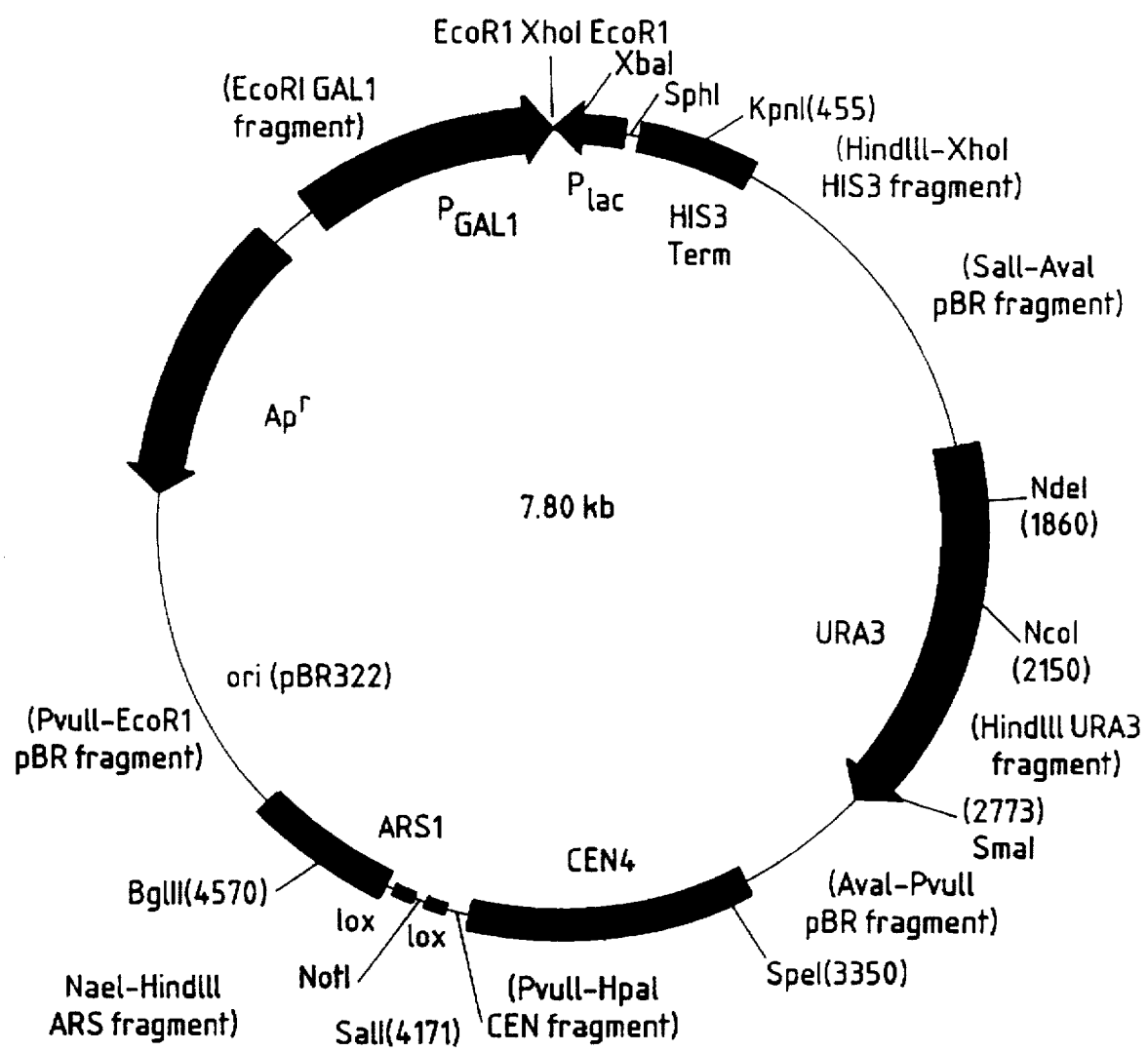
FIG. 3 shows a plasmid into which the KAT1 cDNA was cloned during the construction of the library.
Figure 4:
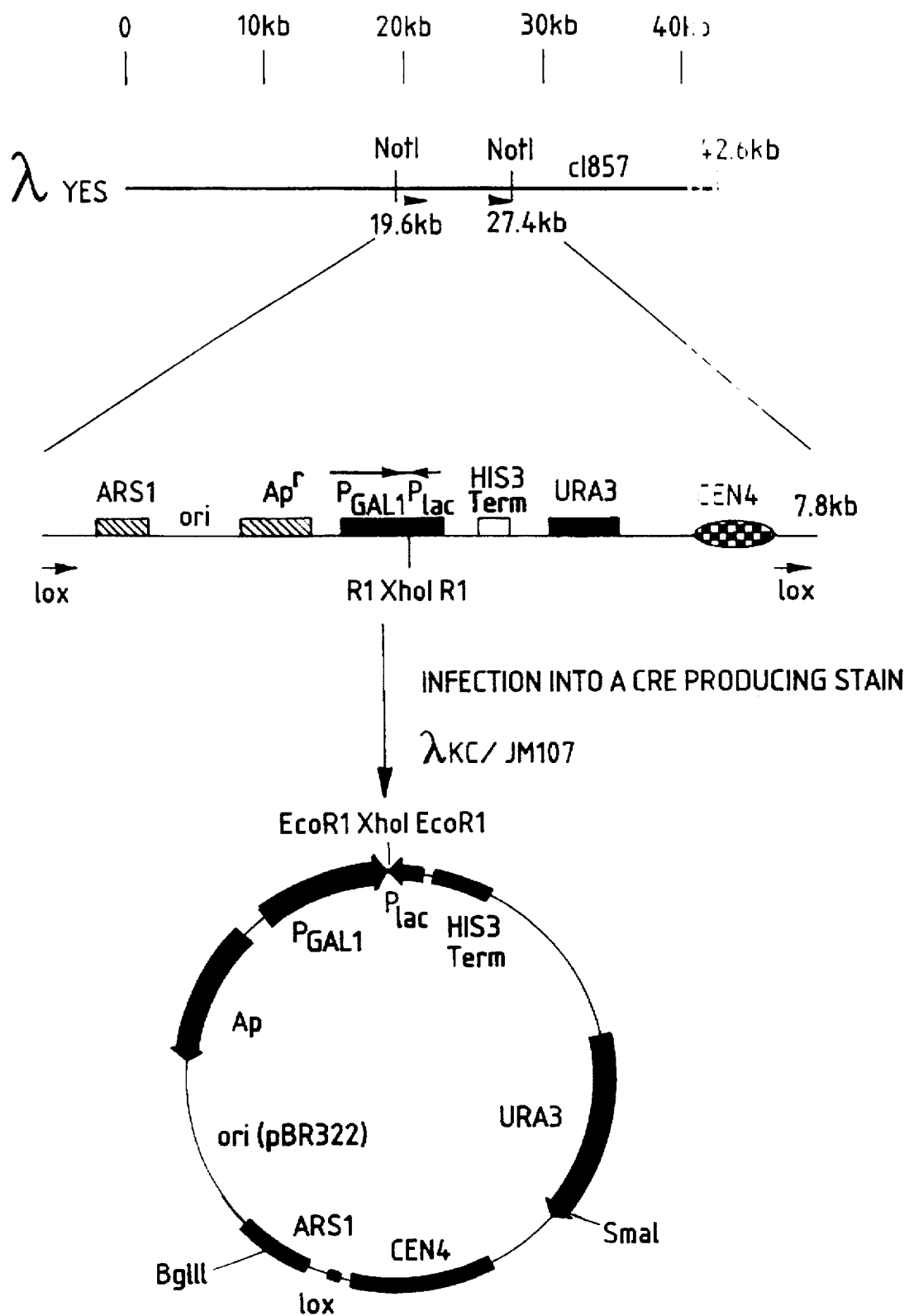
FIG. 4 shows the arabidopsis cDNA expression vector.

The *Arabidopsis thaliana* cDNA library was constructed in the AYES yeast/*E. coli* shuttle vector. (Stanford University, Stanford, Calif.) (Elledge, S. J., Mulligan, J. T., Ranier, S. W., Spottswood, M. and Davis, R. W. (1990) Proc. Natl. Acad. Sci. USA 88, 1731–1735) (hereby incorporated by reference). See FIGS. 3 and 4. This library was made from mRNA extracted from leaves, shoots, stems and flowers of plants at all stages of development (Elledge et al., infra.).

The λ Yes vector is a multifunctional vector. It is capable of replicating as a lambda phage, a plasmid lysogen in *E. coli*, or as a centromere plasmid in yeast. The plasmid part of the vector can be automatically looped out of the lambda phage by site specific recombination using the cre protein and lox sites in the vector (Sternberg, et al. 1983. In Mechanisms of DNA Replication and Recombination. UCLA Symposia on Molecular and Cellular Biology. Vol. 10, pp. 671–684; Sauer and Henderson. 1988. Gene 70: 331–41). The cDNAs are inserted nondirectionally. In one direction, they can be expressed from the *E. coli* lac promoter, with a ribosome binding site and an ATG between the promoter a cloning site. In the other direction, they can be expressed from the yeast gall promoter, and are followed by a yeast transcription termination site. A rough map of the vector is shown on the next page. The selectable markers are Amp resistance in *E. coli* and URA3 in yeast.

The cDNAs are inserted into an XhoI site flanked by EcoRI sites. In theory, the XhoI sites should be regenerated during the cloning. Occasionally, an XhoI site may be missing and the insert must be excised with EcoRI.

Library: PolyA purified mRNA was prepared from the above-ground parts of Arabidopsis plants which varied in size from those which had just opened their primary leaves to plants which had bolted and were flowering. A library of 10 million independent recombinants was amplified as lytic phages on plates. Approximately 90–95% of the clones in the amplified library contain inserts, and the titer is $6.2 \times 10^9$ per ml, a typical titer for this vector.

Storage. The amplified phage stock is in LB with 7% DMSO. The lambda is stable for several weeks at room temperature.

Propagation and Screening. The phage backbone is lambda gt6. It can be treated as a standard lambda phage (e.g. grow lytically on LE392 pMC9 to amplify, or on LE392 to screen for expressed proteins). Alternatively, it can lysogenize as an amp resistant plasmid in a strain which expresses the lambda repressor, cI.

Plasmid Recovery. The plasmid part of the vector can be looped out of the lambda by infecting a strain which expresses cre and cI (eg. BNN132 |JM107 lysogenized with λ KC|). Plasmid DNA can be prepared by:

1) Grow BNN132 overnight in LB+maltose (0.2%)+ kanamycin (50 μ/ml).
2) Spin down and resuspend in lambda dil (5M) buffer.
3) Add phage library to an m.o.i. of 0.01, incubate 20 minutes at 37° C.
4) Grow nonselectively for 30 minutes in LB.
5) Plate on LB+ampicillin, grow overnight at 37° C.
6) Scrape plates and do a standard plasmid preparation.

Yeast. The yeast transformation protocol of Burgers and Percival (Analytical Biochemistry 163:391–397) (hereby incorporated by reference).

The library starts out as lambda phage library. Upon induction of the phage (being grown in *E. coli*) the plasmid "pops out" and can then be amplified and harvested from the *E. coli* culture. The KAT1 cDNA is a XhoI fragment inserted at the XhoI site in the vector. Thus, the size of pKAT1 is the vector 7.80 kb) plus the cDNA insert (about 2.24 kb)+10 kb. The EcoR1 XhoI EcoR1 is the "poly-cloning" site. The KAT1 cDNA fragment is inserted into the XhoI site here. The following sequences are contained on the plasmid:

1. $P_{GAL1}$: Promoter region found the yeast GAL1 gene; this sequence promotes expression of the cDNA insert upon growth on galactose as the sole carbon source.
2. $P_{lac}$: promoter from the *E. coli* lac operon; used for conditional expression of cDNAs (cloned in the opposite direction) in *E. coli*.
3. HIS3 Term: sequence containing the transcriptional termination signals from the yeast HIS3 gene; used to ensure termination of the cDNA insert when expressed in yeast.
4. URA3: the yeast URA3 gene; used as the selectable marker to select for presence of the plasmid in ura3 yeast recipient strains.
5. CEN4: sequences encoding the yeast centromere (#IV); used to maintain stability of the plasmid during yeast cell division, i.e., this makes the plasmid function as a "minichromosome".
6. ARS1: this is an "autonomously replicating sequence" that serves as a site of initiation of replication in yeast.
7. ori (pBR322): this is the site of replication initiation that is used when the plasmid is propagated in an *E. coli* host.
8. Ap$^r$: the ampicillin resistance gene that allows selection for the plasmid in *E. coli*.

Expression of the cloned inserts are under control of the inducible GAL1 promoter. The library was introduced into CY162 cells by transformation. Initial selection and subsequent screening of the transformants were carried out on AA-URA to maintain selection for the plasmids. Ura$^+$ transformants were selected on glucose-containing medium supplemented with 100 mM potassium (GLU-URA 100K) and replicaplated to GAL-URA 100K to induce expression of the cloned cDNAs. Following an overnight incubation the transformants were replica plated to GAL-URA containing 7 mM potassium (7K) to identify cDNAs able to confer suppression of the potassium transport-defective phenotype (Trk-) of the recipient cells.

3. DNA Sequencing

Dideoxy sequencing of pKAT1 was performed using SEQUENASE (U.S. Biochemicals) (Sanger, F. et al. Proc. Natl. Acad. Sci. USA 74:5463–67 (1977) (hereby incorporated by reference). Double stranded template DNA was sequenced using specific oligonucleotide primers synthesized at the Northwestern University Biotechnology Facility.

Primers used for sequencing (all represented in 5' to 3' direction of polarity:

For sequencing the noncoding strand:

| GAL1. | TACTTTAACGTCAAGGAG | Sequence Id No. 2 |
|---|---|---|
| GAL2. | CTAAGCTCCGCAAACAC | Sequence Id No. 3 |
| GAL3. | CTTCTAGTTGACAGTC | Sequence Id No. 4 |
| GAL4. | CGGAAGCGAACTAGG | Sequence Id No. 5 |
| GAL5. | CATTGTGCTGGATGT | Sequence Id No. 6 |
| GAL6. | GATGTTCAACCTCGG | Sequence Id No. 7 |
| LAC5inv. | TACTGCGGATAAGCA | Sequence Id No. 8 |
| LAC4inv. | GGATGGGAAGAGTGG | Sequence Id No. 9 |
| LAC3inv. | TAGTGAAACCGCTGG | Sequence Id No. 10 |
| LAC2inv. | ATCCATAGAAGAGCT | Sequence Id No. 11 |
| LAC1inv. | GCATGTATATCTGCA | Sequence Id No. 12 |

For sequencing the coding strand:

| GAL2inv. | GCTGAGTAAATAACT | Sequence Id No. 13 |
|---|---|---|
| GAL3inv. | ATTCGTATTTTCTTA | Sequence Id No. 14 |
| GAL4inv. | TCAAGCCTTGCAAAT | Sequence Id No. 15 |
| GAL5inv. | TGCTTCTTTGAAATT | Sequence Id No. 16 |
| GAL6inv. | AGGTTGGTCATATTTCCAA | Sequence Id No. 17 |
| LAC5 | TTGTTCTTACTGTGA | Sequence Id No. 18 |
| LAC4 | GTCGGAAGTCGGATTCG | Sequence Id No. 19 |
| LAC3 | GGTTGCTTGAGCTGC | Sequence Id No. 20 |
| LAC2 | ACCATCCCAAATGACAT | Sequence Id No. 21 |
| LAC1 | TGTGGAATTGTGAGCGG | Sequence Id No. 22 |

DNA sequence analysis was done using the DNA inspector 11e (Textco, Lebanon, N.H.) and the Genetics Computer Group (GCG, Madison, Wis.) software.

4. Southern Blot Analysis

Two μg of genomic DNA extracted from *A. thaliana* (Columbia ecotype) was digested with EcoR1, electrophoresed on 0.8% agarose and transferred to nylon membrane. The KAT1 probe was prepared by random hexamer [α-32$_p$] dCTP labelling of the 2.2-kb XhoI insert contained in pKAT. Hybridization overnight at 65° C. was followed by three washes at 60° for 15 minutes each in 6×standard saline citrate/0.1% SDS (Feinberg, A. P. and Vogelstein, B. (1983) Anal. Biochem. 132, 6).

RESULTS

An *Arabidopsis thaliana* cDNA library was screened for sequences that suppress the potassium transport defect (Trk- phenotype) of trk1Δ trk2Δ cells (CY162) by conferring growth on potassium-limiting medium. From approximately 40,000 Ura$^+$ transformants, a single clone was obtained that allows growth of CY162 cells on 7 mM potassium, galactose-containing medium (GAL 7K). The cloned plasmid, pKAT1, was recovered by transformation of *E. coli* and reintroduced into CY162 by transformation. This plasmid is assigned ATCC No. 75224. All Ura$^+$ transformants containing pKAT1 were able to grow on GAL 7K.

Southern analysis using the cDNA insert contained in pKAT1 as a probe revealed the presence of homologous sequences in the *A. thaliana* genome.

1. KAT1 Completely Suppresses the Trk- Phenotype of trk1Δ trk2Δ Cells. Wild type (TRK1 and TRK2) *S. cerevisiae* cells are able to grow on media supplemented with 0.2 mM potassium chloride (0.2K);(Gaber, R. F., Styles, C. A. and Fink, G. R. (1988) Mol. Cell. Biol. 8, 2848–2859). To determine the level of KAT1 suppression, colonies of CY162 cells containing pKAT1 were replica plated to GAL 0.2K. pKAT1 conferred growth on GAL 0.2K but not on GLU 0.2K, consistent with the conditional expression of the cDNA. Growth of CY162/pKATL cells on GAL 0.2K was indistinguishable from that of wild-type cells.

2. DNA sequence Analysis Suggests KAT1 Encodes a Potassium Channel. The cDNA sequence in pKAT1 revealed an open reading frame of 2,031 nucleotides capable of encoding a protein of 677 amino acids (78 kD, Sequence Id. No.1). Northern blot analysis, using KAT1 sequences as a probe, detected a 2.2-kb message that was present in very low abundance, indicating that pKAT1 contains a full-length or near full-length cDNA.

EXAMPLE 1

Tetraethylammonium and $Ba^{2+}$ Inhibit KAT1 Function in vivo

Although the ability to suppress the potassium transport deficient phenotype of trk1Δ trk2Δ cells and the structural features inferred from the KAT1 DNA sequence suggested that KAT1 is potassium channel, the inventor further tested this interpretation by testing the effect of tetraethylammonium and $Ba^{2+}$ ions on the function of KAT1. Tetraethylammonium (TEA) and $Ba^{2+}$ are specific inhibitors of many voltage-gated potassium channels and appear to block channel conductance by interacting with sites normally occupied by potassium ion (Hille, B. (1981) Ionic Channels of Excitable Membranes. Sunderland, Mass., Sinauer; Mackinnon, R. And Yellen, G. (1990) Science 250, 276–278; Yellen, G., Jurman, M. E., Abramson, T. and MacKinnon, R. (1991) Science 251, 939–941). This has been further supported by recent experiments in which mutations residing in the region thought to constitute the lining of the channel pore were shown to affect the binding of tetraethylammonium.

Figure 2:
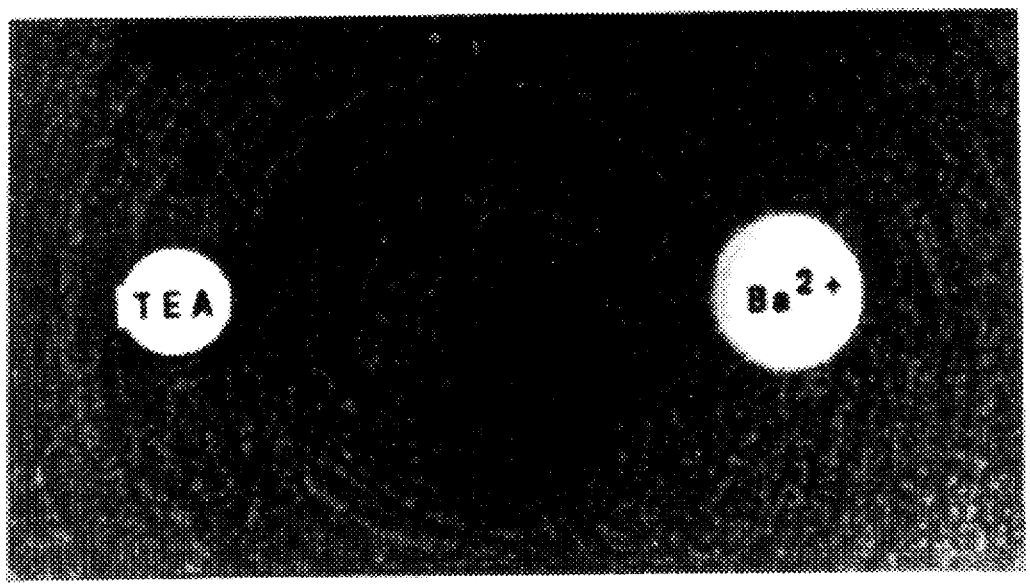
FIG. 2 shows that barium and TEA do not inhibit the growth of CY162/pKAT1 cells when these cells are grown in the presence of a high concentration of potassium.

If KAT1 is a potassium channel, growth of CY162/PKAT1 cells on potassium limited medium would be inhibited by TEA and $Ba^{2+}$. Tetraethylammonium and $Ba^{2+}$ were applied to filter displaced on to lawns of CY162/pKAT1 cells growing on GAL 100K and GAL 0.2K solid media (See FIGS. 1 and 2). Growth of CY162/pKAT1 cells was inhibited by tetraethylammonium and $Ba^{2+}$ on 0.2 mM, but not on 100 mM potassium. Low concentrations of potassium should be added to the screening media. The expression of KAT1 will allow trk1 trk2 cells to grow on very low concentrations of potassium (as low as wild-type TRK1 TRK2 cells). Therefore using a concentration of approximately 0.1 to 0.2 mM potassium would allow even slight inhibition of KAT1 to result in the inhibition of growth of the CY162/pKAT1 cells. In contrast, similar tests using CY162 cells containing TRK1 carried on a centromeric plasmid (pRG295-1) showed no inhibition by these compounds (Gaber, R. F., Styles, C. A. and Fink, G. R. (1988) Mol. Cell. Biol. 8, 2848–2859).

The isolation of KAT1 indicates that *S. cerevisiae* can be used as a powerful and convenient method of isolating potassium channel cDNAs from higher eukaryotes. Other libraries are being screened to determine whether cDNAs encoding human potassium channels can also be isolated using this system. Additionally, the genetically engineered organism of this invention can be used to detect organism the expression of heterologous ion channels. This can be used to screen compounds as potential new herbicides or drugs, as shown in Example 1.

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

---

I claim:

1. A mutant yeast cell transformed with a DNA molecule that encodes a heterologous potassium ion channel former, the expression of which heterologous potassium ion channel former in the transformed cell corrects a deficiency in potassium uptake of the mutant, which deficiency is due to a lack of TRK1 or TRK1 and TRK2 potassium transporters.

2. The mutant yeast of claim 1 wherein the potassium uptake deficiency is characterized by a decreased ability of the yeast to accumulate potassium and grow in an extracellular fluid having a potassium concentration less than about 100 mM.

3. The mutant yeast of claim 1 lacking both the TRK1 and TRK2 potassium transporters.

4. The mutant yeast of claims 1 that is a mutant *Saccharomyces cerevisiae*.

5. Mutated yeast cells designated ATCC No. 74144.

* * * * *